United States Patent [19]

Holmes

[11] Patent Number: 4,830,969

[45] Date of Patent: May 16, 1989

[54] PROCESS FOR THE RAPID AND SIMPLE ISOLATION OF NUCLEIC ACIDS

[75] Inventor: David S. Holmes, Troy, N.Y.

[73] Assignee: The Research Foundation of State University of New York, Albany, N.Y.

[21] Appl. No.: 298,064

[22] Filed: Aug. 31, 1981

[51] Int. Cl.$^4$ .......................... C12N 1/06; C12N 1/08; C07G 17/00; C07K 3/12
[52] U.S. Cl. ..................................... 435/259; 435/264; 435/267; 435/270; 435/272; 435/320; 435/820; 426/60; 536/27; 530/344; 530/412; 530/417; 530/419; 530/423; 530/820
[58] Field of Search ................. 435/99, 267, 262, 259, 435/270, 272, 820, 317, 264; 260/112 R; 536/27, 28; 426/44, 46, 49, 52, 53, 54, 56, 60, 656; 210/737, 530, 344, 412, 417, 419, 423, 820, 821

[56] References Cited

U.S. PATENT DOCUMENTS

| | | | |
|---|---|---|---|
| Re. 25,785 | 6/1965 | Beers | 435/270 |
| 3,585,179 | 6/1971 | Samejima et al. | 435/272 |
| 3,681,195 | 8/1972 | Suekane et al. | 435/259 |
| 3,930,956 | 1/1976 | Juni | 435/259 |
| 3,934,039 | 1/1976 | Cardini et al. | 426/60 |
| 3,959,246 | 5/1976 | Bickoff et al. | 260/112 R |
| 3,991,215 | 11/1976 | Robbins | 426/60 |
| 4,038,143 | 7/1977 | Juni | 435/259 |
| 4,260,644 | 4/1981 | Eriksson et al. | 426/656 |
| 4,338,400 | 7/1982 | Manis et al. | 435/317 |

FOREIGN PATENT DOCUMENTS 2837342 3/1980 Fed. Rep. of Germany ........ 426/60

OTHER PUBLICATIONS

Clewell et al, PNAS USA, 62: 1159–1166 (1969).
Hirt, J. Molec. Biol., 26: 365–369 (1967).
Zasloff et al, Nucleic Acids Research, 5: 1139–1152 (1978).
Colman et al, Eur. J. Biochem., 95: 303–310 (1978).
Birnboim et al, Nucleic Acids Research, 7: 1513–1523 (1979).
Currier et al, Anal. Biochem., 76, 431–441 (1976).
Khoury et al, *Methods in Enzymology*, vol. LVIII, Academic Press, New York, 404, 406–410 (1979).
Longacre et al, *Methods in Enzymology*, 68, Academic Press, New York, 192–199 (1979).

Primary Examiner—Esther M. Kepplinger
Attorney, Agent, or Firm—William J. Crossetta; Michael L. Dunn

[57] ABSTRACT

A process for the separation from other cellular materials of heat agglomeration resistant water soluble nitrogen containing organic compounds such as plasmids, RNA's, mitochondrial DNA's, viral DNA's, chloroplast DNA's, other episomal DNA's and certain proteins. The process comprises heating cellular materials in a solution of lysing agent to lyse the desired cells and to agglomerate water soluble nitrogen containing compounds such as certain chromosomal DNA's which are not resistant to agglomeration; centrifuging the resulting product to remove water soluble agglomerated materials; separating the supernatant liquid and precipitating the water soluble agglomeration resistant organic compounds with a water soluble precipitant. The process also includes separating the agglomeration resistant water soluble nitrogen containing compounds from each other by means of exclusion chromotography.

35 Claims, No Drawings

PROCESS FOR THE RAPID AND SIMPLE ISOLATION OF NUCLEIC ACIDS

BACKGROUND OF THE INVENTION

A) Field of the Invention

This invention relates to the separation of cellular constituents and more particularly relates to the isolation of certain nucleic acids and peptides from other cellular materials. The invention, for example, concerns the isolation of plasmids, RNA's, mitochondrial DNA's, viral DNA's, chloroplast DNA's, other episomal DNA's and certain proteins.

B) History of the Prior Art

Several different procedures have been developed for the isolation of bacterial plasmids and other nucleic acids and proteins from cellular materials. For example, plasmids can be purified from cleared lysates of bacterial cells by centrifuging in density gradients, e.g., cesium chloride and ethidium bromide. Alternatively, nucleic acids such as plasmids can be isolated from bacterial lysates by selective precipitation from high saltsodium dodecyl sulfate systems, by differential alkaline denaturation, by selective extraction in phenol or by hydroxyapatite chromatography. For various references relating to the isolation of nucleic acids from other cellular materials see "Supercoiled Circular DNA-Protein Complex In Escherichia Coli: Purification And Induced Conversion To An Open Circular DNA Form" by D. B. Clewell and D. R. Helinski, *Proceedings of The National Academy of Science USA*, Volume 62, Pages 1159 to 1166; "Selective Extraction of Polyoma DNA from Infected Mouse Cell Cultures" by B. Hirt (1967) *Journal of Molecular Biology*, Volume 26, Pages 365 to 369; "Isolation of Covalently Closed Circular DNA of High Molecular Weight from Bacteria" by T. C. Currier and E. W. Nester (1976), *Analytical Biochemistry*, Volume 76, Pages 431 to 441; "A New Method for the Purification and Identification of Covalently Closed Circular DNA Molecules" by M. Zasloff, G. Ginder and G. Felsenfeld (1978), *Nucleic Acids Research*, Volume 5, Pages 1139 to 1152; "Rapid Purification of Plasmid DNAs by Hydroxyapatite Chromatography" by A. Colman et al (1978), *European Journal of Biochemistry*, Volume 91, Pages 303 to 310; and "A Rapid Alkaline Extraction Procedure for Screening Recombinant Plasmid DNA" by H. C. Birnboim et al (1979) *Nucleic Acids Research*, Volume 7, 1513 to 1523.

The procedures for isolating plasmids and other nucleic acids in protein described in the above references are quite complicated and expensive. Furthermore, in most cases, the procedures for such isolations are extremely time consuming.

The need for isolation of plasmids and other nucleic acids has become critical due to the extremely rapid growth of microbiological analysis and genetic engineering. Isolated plasmids are especially in demand since plasmids provide one of the simplest paths for introducing biological functions into living organisms. In particular, plasmids are cleaved with restriction enzymes followed by the introduction of a nucleic acid grouping at the cleaved site which carries the code for a particular biological function. The plasmid ring is then again closed and the plasmid is introduced into a living organism which then carries out the coded biological function introduced into the plasmid.

BRIEF DESCRIPTION OF THE INVENTION

There is therefore provided, in accordance with the present invention, a process for the separation of agglomeration resistant water soluble nitrogen containing cellular organic compounds from other cellular materials. The organic compounds are selected from nucleic acids and peptides. The method comprises heating cellular material in a solution of lysing agent to a sufficient temperature for a sufficient time to lyse the desired cells and to agglomerate water soluble nitrogen containing compounds which are not resistant to agglomeration, followed by centrifuging the resulting product to remove water insoluble and agglomerated materials. The supernatant liquid is then separated from the agglomerated materials and the water soluble agglomeration resistant organic compounds are precipitated from the supernatant liquid with a water soluble "Agglomeration Resistant Compound", as used herein, means a compound which will not agglomerate in a solution of lysing agent at a temperature below 60° C. Agglomeration resistant water soluble nitrogen containing cellular organic compounds are nucleic acids or peptides which do not have a tendency to interreact to form gels or solids at temperatures below 60° C. in a solution of lysing agent. Such compounds are, in general, believed to be resistant to agglomeration either because of relatively small size compared to other cellular organic compounds or because the compounds are in general less reactive due to reduced availability of reactive sites or both. Plasmids, for example, generally have a closed circular structure which seems to make them less subject to agglomeration at temperatures below 60° C.. It is also known that certain DNA's (deoxyribonucleic acids) such as mitochondrial DNA are circular and coiled. It is therefore believed that certain of such mitochondrial DNA's are also resistant to agglomeration. Certain RNA's (ribonucleic acids) are subject to intramolecular bonding which is believed to render RNA's less subject to aglomeration than some other cellular organic compounds such as chromosomal DNA's. Furthermore, though not universally true, RNA's are generally substantially smaller than chromosomal DNA's as are plasmids, mitochondrial DNA's, most viral DNA's and chloroplasts. Interestingly, the agglomeration resistant water soluble nitrogen containing cellular organic compounds generally include the above mentioned groups, i.e., plasmids, RNA's, mitochondrial DNA's, viral DNA's and chloroplasts.

The agglomeration resistance of these organic compounds is used in accordance with the process of the invention to separate these compounds from other cellular materials.

In accordance with the present invention, the cellular material is heated to a sufficient temperature and for a sufficient time in the presence of a solution of lysing agent to lyse the desired cells and to agglomerate water soluble nitrogen containing compounds which are not resistant to agglomeration. In general, the sufficient temperature is between about 60 and about 105° C., preferably from about 80° to 105° C., and the sufficient time is usually between about 10 seconds and about 3 minutes.

The lysing agent is any suitable compound which will open the cell wall without destroying the desired agglomeration resistant water soluble nitrogen containing cellular organic compounds. Such lysing agents which may used alone or in combination are lysozyme which is a lysing enzyme which is known to weaken and destroy cell wall structures; urea; guanidine hydrochloride and surfactants. The solution of the lysing agent may also contain a chelating agent such as ethylenediamine tetraacetic acid (EDTA) which chelates cellular magnesium reducing the degradation of DNA by the cellular enzyme DNAase. In addition, the solution of the lysing agent usually contains a buffer since DNA is rendered single stranded at extreme alkaline pH and is degraded at extreme acid pH and is least susceptible to degradation by cellular DNAase in the buffer.

In general, the concentrations of components within the solution of lysing agent depends upon the nature of the cells to be lysed and upon the nature of the particular lysing agent and other components being used. Usually when lysozyme is used, as the principle lysing agent, the concentration of lysozyme in the solution is from about 500 micrograms per milliliter to about 1500 micrograms per milliliter. When urea is used as the principle lysing agent, the concentration is usually between about 4 molar and about 10 molar and when guanidine hydrochloride is used, the concentration is usually from about 4 molar to about 6 molar. Surface active agents can also be used alone or in combinations with other lysing agents and their concentration usually varies from about 0.1 microgram per milliliter to about 1 micorgram per milliliter. The quantity of buffer used is usually that quantity required to maintain the pH range between about 5 and about 10. The concentration of a chelating agent, such as ethylenediamine tetraacetic acid (EDTA) when present, is usually from about 20 millimolar to about 100 millimolar.

After the cells are lysed and the solution heated, the solution is centrifuged to remove water insoluble and agglomerated materials. In general, the centrifuging occurs at from about 1000 to about 50,000 g's and usually from between 3000 and 30,000 g's for from about 30 seconds to about 30 minutes and usually from about 3 to about 15 minutes. It is, however, to be understood that any centrifuging parameters may be used which are sufficient to separate water insoluble and agglomerated materials from the liquid.

After centrifuging, the supernatant liquid is removed and the water soluble agglomeration resistant organic compounds are precipitated with a water soluble precipitant. The precipitant is usually an alcohol but may be some other material which will cause precipitation of the agglomeration resistant materials such as high concentrations of salt such as sodium chloride or lithium chloride. The alcohol is usually isopropanol or ethanol. When isopropanol is used, the volume required is usually over about 50% of the volume of the liquid and usually about the same volume as the supernatant liquid. It is to be understood that larger quantities of isopropanol can be used but are usually not necessary. When ethanol is used, a volume of ethanol at least equal to the volume of the liquid must be used and usually the volume of ethanol must be twice the volume of the liquid. It is again understood that excess ethanol can be used but is not usually necessary.

The precipitated water soluble water agglomeration resistant organic compounds, as previously discussed, usually contain substantial quantities of RNA's and, if present in the original cells, usually contains plasmids. If plasmids are present, it has been found they may be immediately restricted without removal of the RNA's even though their percentage usually varies from about less than 1/2% to usually no greater than 10% by weight of the RNA present.

If desired, plasmids can, however, be removed from the RNA's by known methods, e.g., density gradient centrifuging or the plasmids may be separated from the RNA's by a further novel method of the present invention. In accordance with that method, the precipitated agglomeration resistant compounds are resuspended in another liquid, which is usually aqueous. The plasmids are then separated from the RNA by exclusion chromatography when the plasmids are larger than the RNA. If necessary, the RNA may be fragmented so that the fragments are smaller than the plasmids. The RNA is fragmented by any suitable means which is usually by chemical attack with a suitable chemical composition. Such suitable chemical compositions include RNAase enzyme or strong bases, e.g., NaOH or KOH.

The precipitated agglomeration resistant water soluble organic compounds can also be treated with phenol at any time either before or after isolation of compounds within the precipitate. Treatment of the compounds within the precipitate with phenol will remove certain undesirable residual DNA components and protein components within the precipitate which were not removed by the heating and centrifuging steps.

In treating the precipitate with phenol, the precipitate is resuspended in liquid and mixed with phenol, usually in about an equal volume of the liquid, followed by removal of the phenol phase which contains residual chomosomal DNA's and proteins. The phenol desirably is preadjusted to a pH of about 4 with sodium acetate for removal of chromosomal DNA's but may be pH9 to pH10 if only proteins are to be removed.

The following examples serve to illustrate and not limit the present invention. Unless otherwise indicated, all parts and percentages are by weight. All steps were carried out at room temperature unless otherwise specified.

EXAMPLE 1

SEPARATION OF RNA AND PLASMIDS FROM OTHER E. COLI CELLULAR MATERIALS 5 mls of E. Coli strain RR1 were grown overnight in luria broth supplemented with 10 micrograms per milliliter of tetracycline. The broth contained pSC101 plasmids having a gene insert which gives tetracycline resistance. 5 milliliters of these bacteria were grown overnight at 37° to an optical density at about 6,500 angstrom units of about 1.2. The bacteria were drawn down and pelleted by centrifuging at 3000 g's for 5 minutes. The bacteria were then resuspended in 0.35 mls of a solution containing 8% sucrose, 5% Rohm and Hass Co., Triton$^R$ X100 surfactant, 50 millimoles of EDTA and 50 millimoles of Sigma Chemical Company Tris ® buffer to pH 8.0. The solution also contained 25 microliters of 10 milligrams per milliliter stock of freshly prepared lysozyme. The solution was brought to a boil as rapidly as possible over a flame and maintained at the boiling point for from about 15 to about 30 seconds in a boiling water bath. The solution was then centrifuged at 12,000 g's for 10 minutes at room temperature. The supernatant was drawn off of the slightly gelatinous pellet with a pipette and precipitated at −18° C. for 30 minutes by the addition of an equal volume of isopropanol. The precipitate was collected by centrifuging at 12,000 g's for 5 minutes and the precipitate was then separated and resuspended in 100 microliters of water.

The resulting concentration of nucleic acid is found to be about 2000 micrograms per milliliter having an ultraviolet absorption spectrum of relatively clean nucleic acid. 5 to 15 microliters of this solution are sufficient to yield visible DNA bands on a gel after restriction enzyme digestion. About 1 to 2% of the total nucleic acid is plasmid and the majority of the remaining nucleic acid is RNA.

EXAMPLE 2

SEPARATION OF PLASMIDS FROM RNA

The procedure of Example 1. is followed except that the procedure is scaled up to a one liter bacteria culture. The bacteria are pelleted from the culture and resuspended in 70 mls of solution as previously described. The suspended material is processed exactly as described in Example 1. except that the quantities of materials are proportionally larger. Precipitated nucleic acid is pelleted at 12,000 g's for 10 minutes and resuspended in 22 mls of 0.01 molar Tris pH 8.0, followed by the addition of 24.2 g of cesium chloride (CsCl) and 0.4 mls of a 10 mg/ml stock solution of ethidium bromide (EtdBr). The solution is then centrifuged in a Du Pont Sorval® vertical rotor TV865 at 15° C. overnight at 40,000 rpm. After inspection under ultraviolet light, only one band is detectable and it is determined that this corresponds to the plasmid band. The plasmid band is removed and is recentrifuged in cesium chloride-ethidium bromide as described above to remove residual contaminating RNA and main band DNA. The ethidium bromide is then extracted with cesium chloride saturated isopropanol and the plasmid dialyzed against a buffer.

EXAMPLE 3

RECOVERY OF RNA FROM YEAST CELLS 100 mls of yeast cells were grown to a density of about $4 \times 10^7$ cells per ml and then centrifuged at 3000 g/s for 5 minutes at 4° C.. The collected cells were then washed and recentrifuged. The cells were then suspended in 5 milliliters of a lysing solution. The lysing solution is a 7 molar urea, 0.35 molar NaCl, 1 millimolar EDTA and 0.01 molar Tris ® buffer to pH 8.0 solution. 10% sodium dodecyl sulfate (SDS) solution was then added until the lysing solution contains 1% SDS. The suspension was then brought to a boil as rapidly as possible over a naked flame and placed in a boiling water bath for one minute. The solution was centrifuged at 12,000 g's for 5 minutes at room temperature. The supernatant liquid was removed and precipitated with an equal volume of isopropanol at $-18°$ C. for at least 30 minutes. The purified RNA was collected by centrifuging at 12,000 g's for 10 minutes at 4° C..

EXAMPLE 4

RECOVERY OF RNA FROM MOUSE CELLS

Mouse liver cells were grown to a density of $2 \times 10^5$ cells per milliliter. The RNA was recovered from the cells in the same manner as described in Example 3.

EXAMPLE 5

RECOVERY OF RNA FROM SOYBEAN SOLID TISSUES 10 grams of soybeans were ground to a fine powder in liquid nitrogen with a mortar and pestle. The powder was sprinkled onto 10 milliliters of boiling lysing solution as described in Example 3. and stirred while 20% (weight to final volume) SDS solution was added to a final concentration of 1% SDS in the lysing solution. The boiling continued for one minute and RNA was separated as in Example 3. The RNA is contaminated with components of the solid tissue and is further purified with several extractions with a mixture of phenol and chloroform (1:1 volume ratio). The RNA is precipitated from the aqueous phase by adding one-tenth volume of 2 molar sodium acetate solution and two volumes of ethanol and holding the mixture at $-18°$ C. for 1 hour. The purified RNA precipitate is collected by centrifuging at 12,000 g's for 10 minutes at 4° C..

EXAMPLE 6

RECOVERY OF RNA FROM MOUSE LIVER SOLID TISSUE

Example 5. is repeated except 0.4 g of mouse liver is used. EXAMPLE 7 and 8

RECOVERY OF pBR322 AND pSp2 PLASMIDS

E. Coli C600 Strain bacteria were grown as a host for plasmids pBR322 and pSp2 and in each case the plasmids were isolated as follows:

One liter of bacteria were grown overnight in luria broth (10 g tryptone, 5 g yeast extract, 1 g glucose and 5 g NaCl per liter and adjusted to pH of 7.1) supplemented with 10 µg/ml tetracycline and 100 µg/ml ampicillin for plasmid pBR322. The bacteria were then pelleted at 3000 g's for 5 minutes. The pellet was resuspended in the residue of broth after decanting the supernatant and added to 70 ml of an 8 percent sucrose solution (weight to finished aqueous volume) of buffer containing 5% Triton X-100 surfactant, 50 mM EDTA and 50 mM Tris pH 8.0.

50 mg of lysozyme was added and the solution brought to a boil as rapidly as possible in a 500 ml conical flask over a bunsen burner. The solution was maintained at boiling over a moderate flame for about 75 seconds with occasional shaking and immediately centrifuged at 12,000 g's for ten minutes at 4° C..

The supernatant was decanted off the slightly gelatinous pellet and precipitated with an equal volume of isopropanol at $-18°$ C. for 5 minutes. The precipitate was collected by centrifugation at 10,000 g's for 5 minutes.

The precipitate was then resuspended in 4 mls of 0.2N NaOH at room temperature for 10 minutes to dissociate the double stranded contaminating chromosomal DNA into single strands. The solution was then neutralized by addition of 1 ml of 2 N Tris - HCl followed by 0.25 mls of 20% sodium dodecyl sulfate.

The plasmids were then separated from RNA by exclusion chromotography by passing the solution through a $2.5 \times 30$ cm column containing Pharmacia Company Sepharose® 2B beads equilibrated in 0.3M NaCl - 1 mM EDTA - 10 mM Tris pH 8.2 and eluted at room temperature with the same buffer. 7.5 ml fractions were collected and the fractions corresponding to the plasmid DNA were pooled and precipitated at $-18°$ C. overnight with 2 volumes of $-18°$ C. 95% ethanol after addition of 1/10 volume of 2.5 M Na acetate at pH 5.0.

The plasmid precipitate was collected by centrifuging at 10,000 x g for 10 minutes. To further purify the plasmid, the pellet was resuspended in 2 mls of $H_2O$. An equal volume of 100 mM Na acetate pH 4.0–150 mM NaCl buffer solution was added to the plasmids and the mixture was extracted twice at 4° C. with redistilled phenol equilibrated with the same buffer diluted with an equal volume of water.

The aqueous phase was extracted several times with ether to remove the phenol and 1/10 volume of 2.5 M Na acetate pH 5.0 was added to the aqueous phase followed by 2 volumes of cold 95% ethanol. After 15 minutes at $-20°$ C., the purified plasmid precipitate was collected by centrifuging at 10,000 g's for 10 minutes.

EXAMPLE 9

RECOVERY OF PHAGE VIRUS DNA

S7 phage virus was plated on tryptone broth (10 g tryptone and 5 g NaCl per liter) plates using *E. Coli* Ymel as a host. After overnight incubation at 37° C., a large isolated plaque was picked with an applicator stick and the plaque resuspended in 1-2 mls of tryptone broth. One drop of chloroform was added and the mixture vortexed. An overnight culture of *E. Coli* Ymel was diluted 1 to 100 in tryptone broth and allowed to grow one hour at 37° C.. One ml of these cells was added to 0.1 ml of 0.2 M $MgCl_2$ and 0.3 ml of the resuspended plaque. 2.5 mls of tryptone broth (TB) top agar was added and poured onto prewarmed $100 \times 15$ mm TB plates. The plates were incubated at 5-7 hours at 37° C.. The resulting slurry was poured off the plates and centrifuged at 8000 g's for 10 minutes. The supernatant was collected and 2-3 drops of chloroform were added. The suspension was vortexed and refrigerated. This was the infecting stock for bulk propagation of S7 phage virus in the non-permissive host *E Coli* C600. The concentration of phage in the stock was generally $10^{10}$–$10^{11}$ pfu/ml.

An overnight culture of *E Coli* C600 was grown in TB supplemented with 1 μg/ml thiamine and diluted 1/100 with TB +thiamine. The 500 mls of the culture were incubated until the cell density reached $2-3 \times 10^8$ cells/ml (0.2–0.3 $A_{650}$). S7 phage, as prepared above, were added at a multiplicity of infection of 3-5 (viruses per bacterial cell) and an equal volume of pre-warmed TB was added. The culture was shaken vigorously at 37° C. for 4 hours.

The cells were centrifuged at 4000 g's for 5 minutes and the pellet resuspended in about 10 mls of TB. 70 mls of STET buffer was added (8% sucrose - 5% Triton X-100–50 mM EDTA - 50 mM Tris pH 8.0) followed by 50 mg of lysozyme. The solution was brought to a boil as rapidly as possible over a bunsen burner in a 500 ml conical flask and maintained at boiling for 40-60 seconds over a medium flame. The solution was immediately centrifuged at 12,000 g's for 10 minutes. The supernatant was drawn off the gelatinous pellet with a pipette and precipitated by addition of an equal volume of isopropanol at $-20°$ C. for 10 minutes. 40-50 ml of supernatant was drawn off the gelatinous pellet. The fibrous DNA was spooled out on a glass rod immediately following the addition of the isopropanol.

Excess isopropanol was removed from the spooled DNA by squeezing gently against the flask and the DNA was allowed to hydrate on the rod in 6 mls of 1 mM EDTA - 0.01 M TRis pH 8.2 with gentle stirring for 30 minutes. The DNA 'gel' was removed from the glass rod and allowed to completely solublilize with gentle vortexing and heating to 60° C.. The DNA was passed over a Sepharose 2B column ($2.5 \times 30$ cm) equilibrated with 0.3 M NaCl - 1 mM EDTA - 10 mM Tris pH 8.2 and eluted at room temperature with the same buffer. 240 drop fractions (about 7 ml) were collected and the position of the excluded volume containing the S7 phage DNA was monitored by measuring the absorbance at 260 nm. The excluded volume (about fractions 6-9) was pooled and the addition of 2 volumes of $-18°$ C. 95% ethanol was added followed by the addition of 2.5 M Na acetate pH 5.0. S7 phage DNA was recovered by spooling and redissolved in 10 mM Tris - 1 mM EDTA pH 8.2.

What is claimed is:

1. A process for the separation of agglomeration resistant water soluble nitrogen containing cellular organic compounds, selected from the group consisting of water soluble agglomeration resistant nucleic acids, proteins and peptides, from other cellular materials, which process comprises: heating cellular material in a solution of lysing agent to a temperature between 60° and 105° C. for between 10 and 180 seconds to lyse the desired cells and to agglomerate water soluble nitrogen containing compounds which are not resistant to agglomeration; centrifuging the resulting product to remove water insoluble and agglomerated materials; separating the supernatant liquid; and precipitating the water soluble agglomeration resistant organic compounds with a water soluble precipitant.

2. The process of claim 1 wherein the agglomeration resistant organic compounds comprises a protein.

3. The process of claim 1 wherein the agglomeration resistant organic compounds comprise a nucleic acid selected from the group consisting of plasmids, RNA's, mitochondrial DNA's, viral DNA's and chloroplast DNA's.

4. The process of claim 3 wherein the nucleic acid comprises a plasmid.

5. The process of claim 3 wherein the nucleic acid comprises RNA.

6. The process of claim 1 wherein the water soluble precipitant is isopropanol or ethanol.

7. The process of claim 4 wherein the water soluble precipitant is isopropanol or ethanol.

8. The process of claim 5 wherein the water soluble precipitant is isopropanol or ethanol.

9. The process of claim 1 wherein the lysing agent comprises lysozyme.

10. The process of claim 4 wherein the lysing agent comprises lysozyme.

11. The process of claim 5 wherein the lysing agent comprises lysozyme.

12. The process of claim 1 wherein the product is centrifuged at from between 3000 to about 30,000 G's for from about 3 to about 15 minutes.

13. The process of claim 1 wherein the precipitated agglomeration resistant water soluble organic compounds contain plasmids and RNA; the precipitate is separated from the supernatant liquid, resuspended in another liquid, and the plasmids are separated from the RNA by exclusion chromatography.

14. The process of claim 13 wherein the RNA is fragmented prior to being separated from the plasmids by exclusion chromatography.

15. The process of any of claims 1, 2, 3, 4, 5, 6, 7, 8, 9, 10, or 11 wherein the lysing agent comprises a surfactant.

16. The process of any of claims 1, 2, 3, 4, 5, 6, 7, 8, 9, 10, or 11 wherein the lysing agent comprises a chelating agent.

17. The process of any of claims 1, 2, 3, 4, 5, 6, 7, 8, 9, 10, or 11 wherein the lysing agent comprises a buffer to maintain the pH between 5 and 10.

18. The process of claim 1 wherein the precipitated agglomeration resistant water soluble organic compounds contain plasmids and RNA; the precipitate is separated from the supernatant; the precipitate is resuspended in an aqueous liquid to which density gradient chemicals are added and the plasmids are separated from RNA and residual DNA by density gradient centrifuging.

19. The process of claim 1 wherein the precipitated agglomeration resistant water soluble organic compounds are separated from the supernatant liquid; resuspended in an aqueous liquid and treated with phenol to remove residual DNA.

20. A process for the separation of agglomeration resistant water soluble nitrogen containing cellular organic compounds, selected from the group consisting of water soluble agglomeration resistant nucleic acids, proteins and peptides, from other cellular materials, which process comprises: heating cellular material in a solution of lysing agent comprising at least one of urea or guanidinium hydrochloride to a temperature of between about 60° and about 105° C. for between about 10 and about 180 seconds to lyse the desired cells and to agglomerate water soluble nitrogen containing compounds which are not resistant to agglomeration; centrifugating the resulting product to remove water insoluble and agglomerated materials; separating the supernatant liquid; and, precipitating from said liquid the water soluble agglomeration resistant organic compounds with a water soluble precipitant.

21. The process of claim 20 wherein the lysing agent comprises urea.

22. The process of claim 20 wherein the lysing agent comprises guanidinium hydrochloride.

23. The process of claim 20 wherein the agglomeration resistant organic compounds comprise a nucleic acid selected from the group consisting of plasmids, RNA's, mitochondrial DNA's, viral DNA's and chloroplast DNA's.

24. The process of claim 23 wherein the nucleic acid comprises a plasmid.

25. The process of claim 23 wherein the nucleic acid comprises RNA.

26. The process of claim 25 wherein the lysing agent comprises urea.

27. The process of claim 20 wherein the water soluble precipitant is isopropanol or ethanol.

28. The process of claim 20 wherein the lysing agent additionally comprises a surfactant.

29. The process of claim 20 wherein the lysing agent additionally comprises a chelating agent.

30. The process of claim 20 wherein the lysing agent additionally comprises a buffer to maintain pH between about 5 and about 10.

31. The process of claim 20 wherein the product is centrifuged at from between 3000 to about 30,000 G's for from about 3 to about 15 minutes.

32. The process of claim 20 wherein the precipitated agglomeration resistant water soluble organic compounds contain plasmids and RNA; the precipitate is separated from the supernatant liquid, resuspended in another liquid; and, the plasmids are separated from the RNA by exclusion chromotography.

33. The process of claim 32 wherein the RNA is fragmented prior to being separated from the plasmids by exclusion chromotography.

34. The process of claim 20 wherein the precipitated agglomeration resistant water soluble organic compounds contain plasmids and RNA; the precipitate is separated from the supernatant; the precipitate is resuspended in an aqueous liquid to which density gradient chemicals are added; and, the plasmids are separated from RNA and residual DNA by density gradient centrifuging.

35. The process of claim 20 wherein the precipitated agglomeration resistant water soluble organic compounds are separated from the supernatant liquid; resuspended in an aqueous liquid; and, treated with phenol to remove residual DNA.

* * * * *